(12) United States Patent
Tsuruda et al.

(10) Patent No.: US 8,809,615 B2
(45) Date of Patent: Aug. 19, 2014

(54) ADHESIVE PREPARATION

(75) Inventors: Kiyomi Tsuruda, Tosu (JP); Shinji Yamasoto, Tosu (JP); Kouki Shoho, Tosu (JP); Masaru Nakanishi, Tsukuba (JP)

(73) Assignee: Hisamitsu Pharmaceutical Co., Inc., Tosu-shi, Saga (JP)

( * ) Notice: Subject to any disclaimer, the term of this patent is extended or adjusted under 35 U.S.C. 154(b) by 886 days.

(21) Appl. No.: 12/588,721

(22) Filed: Oct. 26, 2009

(65) Prior Publication Data

US 2010/0047328 A1 Feb. 25, 2010

Related U.S. Application Data

(63) Continuation of application No. 12/227,066, filed as application No. PCT/JP2007/065067 on Aug. 1, 2007, now Pat. No. 8,455,376.

(30) Foreign Application Priority Data

Aug. 4, 2006 (JP) ................. P2006-213670

(51) Int. Cl.
*B32B 7/12* (2006.01)
*B32B 15/04* (2006.01)
*C08G 61/02* (2006.01)
*C08J 3/00* (2006.01)
*A61K 6/083* (2006.01)
*A61K 8/72* (2006.01)
*C08L 15/00* (2006.01)
*A61K 6/00* (2006.01)
*C09J 4/00* (2006.01)
*C09J 101/00* (2006.01)
*C09J 201/00* (2006.01)
*A61F 13/00* (2006.01)
*A61F 15/00* (2006.01)
*A61L 15/16* (2006.01)
*A61K 9/70* (2006.01)
*B32B 25/02* (2006.01)

(52) U.S. Cl.
USPC .............. 602/54; 428/343; 428/355 R; 523/1; 523/105; 523/111; 523/118; 523/176; 602/42; 602/52; 602/57; 442/149; 442/250; 424/443; 424/447; 424/449

(58) Field of Classification Search
USPC ....... 602/41–59; 428/343, 355 R; 523/1, 105, 523/111, 118, 176; 424/443, 447, 449; 442/149, 250
See application file for complete search history.

(56) References Cited

U.S. PATENT DOCUMENTS

| | | |
|---|---|---|
| 4,867,150 A | 9/1989 | Gilbert |
| 5,478,567 A | 12/1995 | Nakagawa et al. |
| 6,914,169 B1 | 7/2005 | Oota et al. |
| 6,924,410 B2 | 8/2005 | Tsuruda et al. |
| 7,250,546 B2 | 7/2007 | Tsuruda et al. |
| 2002/0031542 A1 | 3/2002 | Takada et al. |
| 2003/0109819 A1 | 6/2003 | Tsuruda et al. |
| 2003/0149385 A1 | 8/2003 | Tsuruda et al. |
| 2006/0198880 A1 | 9/2006 | Hashimoto et al. |
| 2006/0263420 A1 | 11/2006 | Hirano et al. |
| 2007/0083139 A1 | 4/2007 | Tsuruda et al. |
| 2010/0047328 A1 | 2/2010 | Tsuruda et al. |

FOREIGN PATENT DOCUMENTS

| | | |
|---|---|---|
| EP | 0 674 913 B1 | 10/1995 |
| EP | 1 072 261 A2 | 1/2001 |
| EP | 1238664 A1 | 9/2002 |
| EP | 1284138 A1 | 2/2003 |
| EP | 1676895 A1 | 7/2006 |
| GB | 2045618 A | 11/1980 |
| JP | 54-143517 A | 11/1979 |
| JP | 63-222113 A | 9/1988 |
| JP | 04-057872 A | 2/1992 |
| JP | 06-051244 A | 2/1994 |
| JP | 06-260709 A | 9/1994 |
| JP | 07-226560 A | 8/1995 |
| JP | 07-265353 A | 10/1995 |
| JP | 2816765 B2 | 10/1998 |
| JP | 2000-049406 A | 2/2000 |
| JP | 2000-114630 A | 4/2000 |

| JP | 2000-244417 A | 9/2000 |
| JP | 2001-039864 A | 2/2001 |
| JP | 2001-044557 A | 2/2001 |
| JP | 2001-313433 A | 11/2001 |
| JP | 2001-328935 A | 11/2001 |
| JP | 2003-031879 A | 1/2003 |
| JP | 2003-169823 A | 6/2003 |
| JP | 3499247 B2 | 2/2004 |
| JP | 2004-146681 A | 5/2004 |
| JP | 2006-045101 A | 2/2006 |
| JP | 2007-015963 A | 1/2007 |
| JP | 2007-151916 A | 6/2007 |
| JP | 4664281 B2 | 4/2011 |
| JP | 4705301 B2 | 6/2011 |
| JP | 4927403 B2 | 5/2012 |
| RU | 2 194 496 C2 | 12/1999 |
| WO | 01-68061 A1 | 9/2001 |
| WO | 2005/092265 A1 | 10/2005 |
| WO | 2006/095820 A1 | 9/2006 |

OTHER PUBLICATIONS

Office Action issued on Sep. 22, 2011, in a counterpart MX patent application, 4 pages.
Notice of Allowance issued on Aug. 16, 2011, in a counterpart RU patent application No. 2008144958; 12 pages; in English and Russian.
"Guidance for Industry, Bioanalytical Method Validation", *U.S. Department of Health and Human Services*, May 2001, pp. 1-22, Food and Drug Administration.
Martin, D., et al., "Dermal Absorption of Camphor, Menthol, and Methyl Salicylate in Humans", *Journal of Clinical Pharmacology*, 2004, vol. 44, No. 10, pp. 1151-1157, The American College of Clinical Pharmacology.
Usami, E., "Comparison Study of the Action of Fomentation, with Methyl Salicylate as the Main Component", *Journal of Japan Hospital Pharmacist Association*, vol. 29, No. 9, 1993, pp. 1003-1008.
Miyazaki, M., "Symposium: The 3$^{rd}$ Percutaneous Absorption Type Preparation Symposium, Poster Session 14, The Pharmaceutical Evaluation of Various Shaped Cataplasms", *Therapeutic Research*, vol. 8, No. 1, 1988, pp. 257-258.
Miyazaki, M., "The Pharmaceutical Investigation of Shaped Cataplasm", *Hospital Pharmacy*, vol. 14, No. 3, 1988, pp. 192-197.
Valdez, J.S., et al., "Sensitive and Selective Gas Chromatographic Methods for the Quantitation of Camphor, Menthol and Methyl Salicylate from Human Plasma", *Journal of Chromatography B*, vol. 729, No. 1-2, 1999, pp. 163-171, Elsevier Science B.V.
Tsuboi, M., "Symposium: The 1$^{st}$ Percutaneous Absorption Type Preparation Symposium, the Fundamentals of Shaped Cataplasm, the Alteration of Dermal Bioactivity by a Patch for External Use and the Percutaneous Absorption of the Base Component of Cataplasm (Salicylate Esters)", *Therapeutic Research*, vol. 3, No. 6, 1985, pp. 987-993.
Suzuki, et al., JP 2006-045101 A, (2006), machine translation, 14 pages.
Office Action issued on Sep. 28, 2011, in a counterpart US patent application, 16 pages.
PCT Forms: PCT/IB/338 Notification of Transmittal of Translation of the International Preliminary Report on Patentability, one page; PCT/IPEA/409 Translation of the International Preliminary Report on Patentability, ten pages; date of mailing: Feb. 19, 2009, from the International Bureau of the Patent Cooperation Treaty.
Official Action issued for JP Patent Application No. P2007-085182 on Oct. 30, 2012.
Celanese Acetate, "Complete Textile Glossary", 2001, p. 40.
Search Report issued in European Patent Application No. 07791748.2 dated Oct. 2, 2013, 6 pages.

*Primary Examiner* — Patricia Bianco
*Assistant Examiner* — Brandon L Jackson
(74) *Attorney, Agent, or Firm* — Nath, Goldberg & Meyer; Joshua B. Goldberg

(57) ABSTRACT

An adhesive preparation comprising a stretchable support and an adhesive layer laminated on at least one side of the support, wherein
the stretchable support comprises a interlock woven fabric subjected to crimping processing,
the adhesive layer contains 10% by mass or more of methyl salicylate with respect to the total mass of the layer,
the whole adhesive preparation has moisture permeability of 1 to 350 g/m$^2$·24 hr measured at a temperature of 40° C. and a relative humidity of 90%, and
the methyl salicylate has a plasma AUC$_{0-24}$ ranging from 3.0 to 60.0 ng·hr/mL in terms of a mean±standard deviation, and salicylic acid as a metabolite of the methyl salicylate has a plasma AUC$_{0-24}$ ranging from 5000 to 13000 ng·hr/mL in terms of a mean±standard deviation, when the adhesive preparation is applied to a human skin for 8 hours such that an application amount of the adhesive layer applied is 50 to 300 g/m$^2$ and a contact area is 280 cm$^2$.

12 Claims, 3 Drawing Sheets

ADHESIVE PREPARATION

This is a Continuation Application of U.S. patent application Ser. No. 12/227,066, filed Nov. 6, 2008, which was filed under 35 U.S.C. 371 as a national stage of PCT/JP2007/065067, filed Aug. 1, 2007, the content of each of which is hereby incorporated by reference in its entirety.

TECHNICAL FIELD

The present invention relates to an adhesive preparation containing methyl salicylate.

BACKGROUND ART

Heretofore, anti-inflammatory analgesics for external use, which are supplemented with a non-steroidal anti-inflammatory agent such as a salicylic acid-based compound (e.g., methyl salicylate), indomethacin, diclofenac, or ketoprofen, and with l-menthol as a cooling agent, have been frequently used, irrespective of patches substantially free from moisture in an adhesive or poultices containing moisture in an adhesive. However, adhesive preparations containing methyl salicylate have room for improvement in terms of analgesic effects, even though they are very frequently used.

Non-Patent Documents 1 and 2 have reported that the plasma concentration of methyl salicylate was measured, when an adhesive preparation supplemented with methyl salicylate was applied to a human. Of these documents, Non-Patent Document 1 discloses that the plasma concentration of methyl salicylate hardly rose, when two pieces of adhesive preparation supplemented with 74.88 mg/piece of methyl salicylate were applied to a human, and that a plasma concentration of methyl salicylate of approximately 30 ng/mL was obtained, when eight pieces of such adhesive preparation were applied to a human.

Non-Patent Document 1: Journal of Clin Pharmacol 2004; 44: 1151-1157

Non-Patent Document 2: Journal of chromatography. B, Biomedical sciences and applications, Jun. 11, 1999; 729 (1-2): 163-71

DISCLOSURE OF THE INVENTION

As is evident from the description of Non-Patent Document 1, a plasma concentration serves as an index for percutaneous absorption, and therefore, previous adhesive preparations supplemented with methyl salicylate exhibited insufficient percutaneous absorption and as a result, did not produce sufficient anti-inflammatory analgesic effects.

For obtaining sufficient percutaneous absorption, it is possible, as described in Non-Patent Document 1, that plural adhesive preparations are simultaneously applied or an adhesive preparation is applied to a large area. However, such an approach is not practical in consideration of the burdens on the skin. On the other hand, it is also possible that an adhesive preparation is supplemented with a high concentration of methyl salicylate. However, methyl salicylate is a volatile substance. Therefore, even if a usual adhesive preparation is supplemented with a high concentration of methyl salicylate, it is difficult to maintain the methyl salicylate at a high concentration in the adhesive preparation, due to volatilization. Moreover, methyl salicylate itself acts as a plasticizer. Therefore, even if an adhesive preparation is supplemented with a large amount of methyl salicylate, the flexibility of the adhesive preparation, particularly, adhesive layer therein, may be altered due to subsequent volatilization. Such an adhesive preparation has the problem that the flexibility or application properties of the adhesive preparation become difficult to control.

The present invention has been completed in consideration of the problems described above. Specifically, an object of the present invention is to provide an adhesive preparation, which, even though it contains a high concentration of methyl salicylate in an adhesive, can maintain the methyl salicylate at a high concentration in the adhesive, has favorable application properties, and is capable of being stably percutaneously absorbed.

The present inventors have conducted diligent studies to attain the object and have consequently completed the present invention by finding out that an adhesive preparation comprising an adhesive layer containing 10% by mass or more of methyl salicylate, which is formed on a particular stretchable support, wherein the whole adhesive preparation has particular moisture permeability has excellent application properties and can maintain the sufficient blood concentrations of the methyl salicylate and its metabolite salicylic acid.

Specifically, the present invention provides an adhesive preparation comprising a stretchable support and an adhesive layer laminated on at least one side of the support, wherein the stretchable support comprises a interlock woven fabric subjected to crimping processing, the adhesive layer contains 10% by mass or more of methyl salicylate with respect to the total mass of the layer, the whole adhesive preparation has moisture permeability of 1 to 350 $g/m^2 \cdot 24$ hr measured at a temperature of 40° C. and a relative humidity of 90%, and the methyl salicylate has a plasma $AUC_{0-24}$ ranging from 3.0 to 60.0 ng·hr/mL in terms of a mean±standard deviation, and salicylic acid as a metabolite of the methyl salicylate has a plasma $AUC_{0-24}$ ranging from 5000 to 13000 ng·hr/mL in terms of a mean±standard deviation, when the adhesive preparation is applied to a human skin for 8 hours such that an application amount of the adhesive layer is 50 to 300 $g/m^2$ and a contact area is 280 $cm^2$. In this context, the plasma concentrations of the drug and the metabolite are measured according to, for example, the guideline of FDA (U.S. Food and Drug Administration) (Guidance for Industry=Bioanalytical Method Validation). It is preferred that the range from the maximum to minimum values of the numerical value in a population in which the $AUC_{0-24}$ has been measured should be 3 to 200 ng·hr/mL (preferably, 3 to 140 ng·hr/mL, more preferably 6 to 60 ng·hr/mL) for the plasma $AUC_{0-24}$ of the methyl salicylate and 2500 to 25000 ng·hr/mL (preferably, 2800 to 25000 ng·hr/mL, more preferably 2900 to 24000 ng·hr/mL) for the plasma $AUC_{0-24}$ of the salicylic acid as a metabolite of the methyl salicylate. The numerical range of the "mean±standard deviation" used herein means that individual data distribution follows normal distribution, and approximately 68% thereof falls within the numerical range of the "mean±standard deviation". More specifically, it means that approximately 95% of individual data falls within the numerical range of the "mean±double standard deviations".

The adhesive preparation of the present invention has the particular support and moisture permeability within the particular range. Therefore, the adhesive preparation of the present invention has good skin following properties and can favorably maintain application properties. In addition, the adhesive preparation of the present invention, even though it is supplemented with the high concentration of methyl salicylate, suppresses the volatilization of the methyl salicylate and is capable of being stably percutaneously absorbed.

According to the adhesive preparation of the present invention, the plasma $AUC_{0-24}$ of methyl salicylate and its metabolite salicylic acid, which is a substance that exhibits anti-inflammatory analgesic effects can be maintained within particular ranges, and local anti-inflammatory analgesic effects can be improved sufficiently. Specifically, according to the adhesive preparation of the present invention, the methyl salicylate can have a plasma $AUC_{0-24}$ ranging from 3.0 to 60.0 ng·hr/mL in terms of a mean±standard deviation, and the salicylic acid can have a plasma $AUC_{0-24}$ ranging from 5000 to 13000 ng·hr/mL in terms of a mean±standard deviation, when the adhesive preparation is applied to a human skin for 8 hours such that an application amount of the adhesive layer is 50 to 300 $g/m^2$ and a contact area is 280 $cm^2$.

Moreover, according to the adhesive preparation of the present invention, the plasma $C_{max}$ of the methyl salicylate and the salicylic acid can be maintained within particular ranges, and local anti-inflammatory analgesic effects can be improved sufficiently. Specifically, according to the adhesive preparation of the present invention, the methyl salicylate can have a plasma $C_{max}$ ranging from 2.0 to 40.0 ng/mL in terms of a mean±standard deviation, and the salicylic acid can have a plasma $C_{max}$ ranging from 700 to 2000 ng/mL in terms of a mean±standard deviation, when the adhesive preparation is applied to a human skin for 8 hours such that an application amount of the adhesive layer is 50 to 300 $g/m^2$ and a contact area is 280 $cm^2$. In this context, the plasma concentrations of the drug and the metabolite are measured according to, for example, the guideline of FDA (U.S. Food and Drug Administration) (Guidance for Industry=Bioanalytical Method Validation). It is preferred that the range from the maximum to minimum values of the numerical value in a population in which the $C_{max}$ has been measured should be 2 to 150 ng/mL (preferably, 2 to 130 ng/mL, more preferably 2 to 125 ng/mL) for the plasma $C_{max}$ of the methyl salicylate and 300 to 4500 ng/mL (preferably, 300 to 3000 ng/mL, more preferably 450 to 2700 ng/mL) for the plasma $C_{max}$ of the salicylic acid as a metabolite of the methyl salicylate.

It is preferred that the adhesive layer of the present invention should contain 1% by mass or more of l-menthol with respect to the total mass of the adhesive layer. l-menthol serves as a cooling agent, while l-menthol itself has analgesic effects and also has the effect of promoting the percutaneous absorption of the active ingredient. Therefore, l-menthol is contained in the range described above and can thereby also exhibit local analgesic effects, in addition to salicylic acid. Furthermore, the local percutaneous absorption of the methyl salicylate is promoted. Therefore, local anti-inflammatory analgesic effects can be further improved.

According to such an adhesive preparation, the plasma $AUC_{0-24}$ and $C_{max}$ of l-menthol can be maintained within particular ranges, and local anti-inflammatory analgesic effects can be further improved. Specifically, according to the adhesive preparation, the l-menthol can have a plasma $AUC_{0-24}$ ranging from 30.0 to 130.0 ng·hr/mL in terms of a mean±standard deviation and a plasma $C_{max}$ ranging from 5.0 to 20.0 ng/mL in terms of a mean±standard deviation, when the adhesive preparation is applied to a human skin for 8 hours such that an application amount of the adhesive layer is 50 to 300 $g/m^2$ and a contact area is 280 $cm^2$. In this context, the plasma concentrations of the drug and the metabolite are measured according to, for example, the guideline of FDA (U.S. Food and Drug Administration) (Guidance for Industry=Bioanalytical Method Validation). It is preferred that the range from the maximum to minimum values of the numerical value in a population in which the plasma $AUC_{0-24}$ and $C_{max}$ of the l-menthol have been measured should be 10 to 300 g·hr/mL (preferably, 10 to 280 ng/mL, more preferably 13 to 220 ng·hr/mL) for the plasma $AUC_{0-24}$ and 1 to 60 ng/mL (preferably, 2 to 55 ng/mL, more preferably 2 to 30 ng/mL) for the plasma $C_{max}$.

For the adhesive preparation of the present invention, it is preferred that the interlock woven fabric as the support should have a weight of 80 to 150 $g/m^2$. If the weight falls within this range, an adhesive base does not seep through the stitches of a knitted fabric when the adhesive is applied to the knitted fabric. Furthermore, anchoring properties with the adhesive base can be maintained. Thus, application properties as the adhesive preparation can be further improved.

For the adhesive preparation of the present invention, it is preferred that the adhesive layer should contain a thermoplastic elastomer. The thermoplastic elastomer is easy to handle and causes a relatively low irritation to the skin. Therefore, it is preferably used. It is preferred that the thermoplastic elastomer should be one kind or two or more kinds selected from the group consisting of a styrene-isoprene-styrene block copolymer, a styrene-butadiene-styrene block copolymer, a styrene-isoprene rubber, a styrene-butadiene rubber, polyisoprene, polybutadiene, and polyisobutylene.

It is preferred that a content of the thermoplastic elastomer should be 25% by mass to 50% by mass with respect to the total mass of the adhesive layer. If the content falls within this range, the cohesion and shape retention of the adhesive layer can be favorably maintained. Accordingly, favorable application properties can be obtained.

Since appropriate tackiness and flexibility can be imparted to the adhesive layer, it is preferred that the adhesive layer should contain a rosin-based resin and/or a petroleum-based resin as a tackifier. It is preferred that a content of the tackifier should be 10% by mass to 30% by mass with respect to the total mass of the adhesive layer. If the content falls within this range, the adhesion of the adhesive layer can be maintained in an appropriate range. Furthermore, the resulting adhesive preparation can be prevented from coming off when applied to the skin or from causing pain when peeled off.

According to the present invention, the present invention provides an adhesive preparation, which, even though it contains a high concentration of methyl salicylate in an adhesive, can maintain the methyl salicylate at a high concentration in the adhesive, has good skin following properties, few irritations to the skin, and favorable application properties, suppresses the volatilization of the methyl salicylate, and is capable of being stably percutaneously absorbed.

BEST MODE FOR CARRYING OUT THE INVENTION

Figure 1:
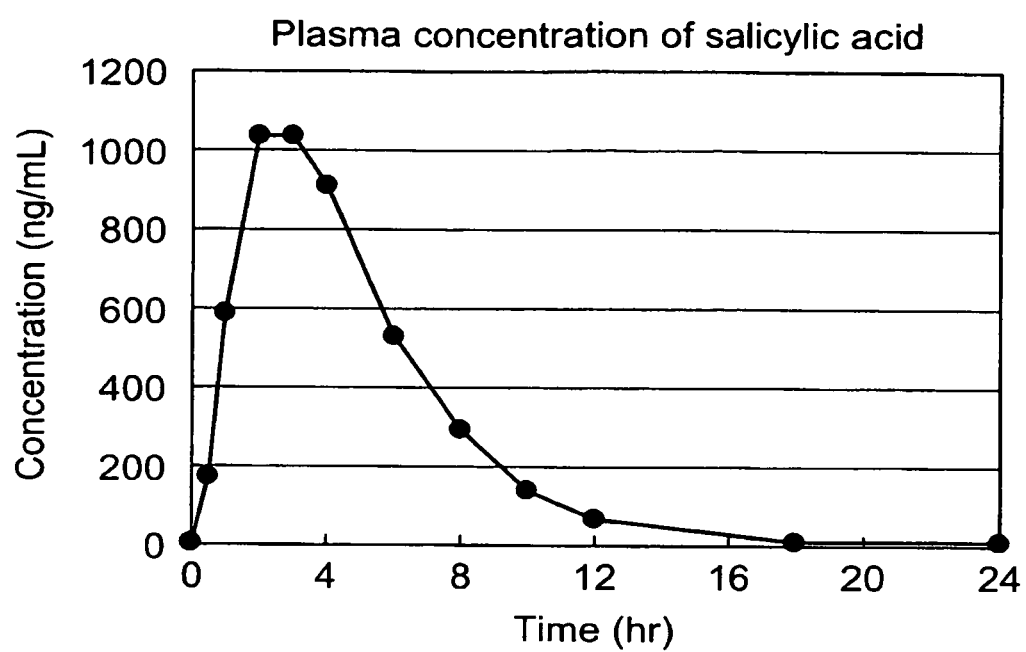
FIG. 1 is a diagram showing changes in the plasma concentration of salicylic acid over time.

An adhesive preparation of the present invention is an adhesive preparation comprising a stretchable support and an adhesive layer laminated on substantially the whole surface on at least one side of the support.

First, the stretchable support will be described.

The support used in the present invention is an interlock woven fabric (including a knitted fabric) subjected to crimping processing and is preferably an interlock woven fabric (knitted fabric) subjected to crimping processing that has two or more tiers of a multifilament yarn of a thermoplastic synthetic resin. This knitted fabric is sufficiently stretchable. Therefore, the adhesive preparation of the present invention can firmly follow the skin without coming off or dropping off when locally applied, for example, applied to the limbs such as the elbow or the knee. Examples of a preferable material for this knitted fabric include those comprising one kind of or a combination of two or more kinds of polyester-based, polyethylene-based, and polypropylene-based materials. Among others, a polyester-based woven fabric (including a knitted fabric) comprising polyethylene terephthalate less interacting with a drug is more preferable.

For the knitted fabric as the support, it is preferred that its weight (weight per unit area) should be 80 to 150 g/m$^2$. If the weight falls within this range, an adhesive base (which refers to an ingredient having adhesion, among ingredients constituting the adhesive layer; the same holds true for the description below) does not seep through the stitches of the knitted fabric when the adhesive described later is applied to the knitted fabric. Furthermore, anchoring properties with the adhesive base can be maintained. Thus, the adhesion of the adhesive preparation can be improved.

Moreover, it is preferred that the support should have a longitudinal modulus (modulus in the major axis direction) of 2 to 12 N/5 cm and a lateral modulus (modulus in the minor axis direction) of 2 to 8 N/5 cm measured according to the method of JIS L1018. When the support has a modulus lower than 2 N/5 cm, the adhesive tends to seep into the stitches of the knitted fabric due to the stretched knitted fabric when applied thereto, and functions as the adhesive preparation tend to be reduced. On the other hand, when the support has a longitudinal modulus higher than 12 N/5 cm or a lateral modulus higher than 8 N/5 cm, the resulting support is poorly stretchable. Furthermore, such an adhesive preparation is less likely to follow skin expansion when applied to a bend of the body.

Next, the adhesive layer will be described.

The adhesive layer of the present invention comprises an adhesive. This adhesive contains a drug methyl salicylate and an adhesive base as essential ingredients. The content of the methyl salicylate in the adhesive layer is 10% by mass or more with respect to the total mass of the adhesive layer. The adhesive preparation of the present invention supplemented with this concentration of methyl salicylate has the predetermined support and the predetermined moisture permeability shown later. Accordingly, the adhesive preparation of the present invention can have the plasma concentration of each drug described later and can thereby produce sufficient local analgesic effects. Since the plasma concentration of the drug can be maintained more preferably, it is preferred that the content of the methyl salicylate should be 10 to 15% by mass, more preferably 10 to 12% by mass, with respect to the total mass of the adhesive layer.

Moreover, for the adhesive preparation of the present invention, it is preferred that the adhesive layer should further contain 1% by mass or more of l-menthol as a drug contained therein. l-menthol itself has analgesic effects and also has the effect of promoting the percutaneous absorption of the methyl salicylate. Therefore, l-menthol is contained in this range, and thereby, local anti-inflammatory analgesic effects can be further improved.

Examples of the adhesive base include thermoplastic elastomer-based adhesives, acrylic adhesives, rubber-based adhesives (except for the former two adhesives), polyurethane-based adhesives, silicone-based adhesives, and adhesives comprising a mixture thereof.

Examples of the thermoplastic elastomer-based adhesives include those containing a thermoplastic elastomer and a tackifier. When the thermoplastic elastomer itself has adhesion, the use of the tackifier is not essential. The thermoplastic elastomer that can be used in the thermoplastic elastomer-based adhesives can be exemplified by styrene-isoprene-styrene block copolymers, styrene-butadiene-styrene block copolymers, polyvinyl acetate, ethylene-vinyl acetate copolymers, styrene-isoprene rubbers, styrene-butadiene rubbers, polyisoprene, and polybutadiene. Of them, a thermoplastic elastomer-based adhesive comprising a styrene-isoprene-styrene block copolymer is preferable from the viewpoint of cohesiveness, weather resistance, aging resistance, and chemical resistance.

Examples of the styrene-isoprene-styrene block copolymers include Cariflex TR-1107, TR-1111, TR-1112, and TR-1117 (all from Shell Chemicals Ltd.), Quintac 3530, Quintac 3421, and Quintac 3570C (all from Zeon Corp.), JSR SIS-5000 and JSR SIS-5002 (all from Japan Synthetic Rubber Co., Ltd.), Krayton D-KX401CS and D-1107CU (all from Shell Chemicals Ltd.), and Solprene 428 (Phillip Petroleum Company). One kind of or a combination of two or more kinds of them can be used.

Examples of the acrylic adhesives include an adhesive in which at least one kind of (meth)acrylic monomer such as (meth)acrylic acid, 2-ethylhexyl (meth)acrylate, octyl (meth)acrylate, methyl (meth)acrylate, butyl (meth)acrylate, hydroxyethyl (meth)acrylate, glycidyl (meth)acrylate, and methoxyethyl (meth)acrylate is polymerized or copolymerized at a monomer ratio that exerts adhesion at a use temperature for the adhesive preparation. A monomer (e.g., vinyl acetate) other than the (meth)acrylic monomers can be used as a monomer for the copolymerization. The acrylic adhesives themselves usually have adhesion. Therefore, the addition of a tackifier is not essential. However, tackiness, the modulus of elasticity, or the like may be controlled by the addition of a tackifier.

The acrylic adhesive is preferably a copolymer comprising a high-Tg monomer (monomer having a glass transition temperature higher than room temperature when homopolymerized) and a low-Tg monomer (monomer having a glass transition temperature lower than room temperature when homopolymerized) in combination. (Meth)acrylic acid which has polarity and contributes to high adhesiveness is suitable as the high-Tg monomer. (Meth)acrylic acid ester containing an alkyl group having 4 to 12 (preferably, 4 to 8) carbon atoms (a hydrogen atom in the alkyl group may be substituted by a hydroxy group) is suitable as the low-Tg monomer.

Examples of the rubber-based adhesives include natural rubber-based adhesives and polyisobutylene-based adhesives. The natural rubber-based adhesives comprise a natural rubber and a tackifier. The polyisobutylene-based adhesives comprise polyisobutylene having various molecular weights and may be supplemented with various additives, if necessary. It is particularly preferred that the adhesive comprising polyisobutylene should be used as a mixture with a styrene-isoprene-styrene block copolymer.

Examples of the polyurethane-based adhesives include aliphatic polyurethane adhesives and aromatic polyurethane adhesives. Examples of the silicone-based adhesives include an adhesive containing a crude rubber of silicone such as a polydimethylsiloxane polymer, polymethylvinylsiloxane, or polymethylphenylsiloxane and an MQ resin (silicone resin with a three-dimensional structure comprising an "M unit" such as $(CH_3)_2SiO_{1/2}$ and a "Q unit" such as $SiO_2$).

It is preferred that the content of the adhesive base (the total amount of the adhesive base and the tackifier, if any) should be 35 to 80% by mass, more preferably 40 to 75% by mass, with respect to the total mass of the adhesive layer, from the viewpoint of the cohesion and shape retention of the adhesive layer. When the adhesive base contains a tackifier, it is preferred that the content of the ingredient (thermoplastic elastomer or natural rubber) except for the tackifier should be 25 to 50% by mass, more preferably 30 to 45% by mass, with respect to the total mass of the adhesive layer. If the content falls short of the lower limit described above, elasticity tends to be weakened. Alternatively, if the content exceeds the upper limit described above, shape retention tends to be poor.

The thermoplastic elastomer-based adhesives or the rubber-based adhesives as the adhesive base usually contain a tackifier for exerting adhesion. A tackifier can be added even to an adhesive base having adhesion by itself without the addition of the tackifier. Such a tackifier is preferably a rosin-based resin and/or a petroleum-based resin. Examples of the rosin-based resin include natural resin rosin, denatured rosin, rosin ester (e.g., rosin glycerin ester or rosin pentaerythritol ester), and hydrogenated rosin ester (e.g., hydrogenated rosin glycerin ester or hydrogenated rosin pentaerythritol ester). Among others, hydrogenated rosin ester is preferable from the viewpoint of skin irritation and aging resistance. Hydrogenated rosin glycerin ester is particularly preferable. Specific examples of such a rosin-based resin include Ester Gum H and Pinecrystal KE-100 and KE-311 (all from Arakawa Chemical Industries, Ltd.) and Foral 85, Foral 105, Staybelite Ester 7, and Staybelite Ester 10 (all from Rika-Hercules, Inc.). One kind of or a combination of two or more kinds of them can be used.

Moreover, examples of the petroleum-based resin include C5 synthetic petroleum resins (e.g., copolymers comprising at least two kinds of isoprene, cyclopentadiene, 1,3-pentadiene, and 1-pentene; copolymers comprising at least two kinds of 2-pentene and dicyclopentadiene; and resins mainly composed of 1,3-pentadiene), C9 synthetic petroleum resins (e.g., copolymers comprising at least two kinds of indene, styrene, methylindene, and α-methylstyrene), and dicyclopentadiene-based synthetic petroleum resins (e.g., copolymers with isoprene and/or 1,3-pentadiene mainly composed of dicyclopentadiene). C9 synthetic petroleum resins are preferable from the viewpoint of weather resistance and compatibility with the adhesive base.

Moreover, examples of the petroleum resin from the viewpoint of another classification include alicyclic petroleum resins (alicyclic hydrocarbon resins such as alicyclic saturated hydrocarbon resins), alicyclic hydrogenated petroleum resins, aliphatic petroleum resins (aliphatic hydrocarbon resins), aliphatic hydrogenated petroleum resins, and aromatic petroleum resins. Alicyclic petroleum resins and alicyclic hydrogenated petroleum resins are preferable from the viewpoint of adhesion, compatibility with the adhesive base, and aging resistance. Alicyclic hydrogenated petroleum resins are particularly preferable. Specific examples of such a petroleum-based resin include Arkon P70, Arkon P-90, Arkon P-100, Arkon P-115, and Arkon P-125 (All from Arakawa Chemical Industries, Ltd.) and Escoretz 8000 (Esso Chemical Ltd.). One kind of or a combination of two or more kinds of them can be used.

The adhesive may further contain, in addition to the rosin-based resin and/or the petroleum-based resin, other kinds of tackifiers such as terpene-based resins, phenol-based resins, and xylene-based resins.

The adhesive layer is supplemented with 10% by mass to 30% by mass, preferably 15% by mass to 25% by mass of the tackifier, with respect to the total mass of the adhesive layer. If the content described above is less than 10% by mass, physical properties of adhesion are easily reduced, and the resulting adhesion preparation easily comes off when applied. If the content exceeds 30% by mass, the resulting adhesion preparation might cause an irritation to the skin and might cause pain when peeled off.

The adhesive layer in the adhesive preparation of the present invention may contain an absorption promoter, in addition to the drug, the adhesive base, and the tackifier. Such an absorption promoter may be a compound whose effect of promoting absorption into the skin has heretofore been recognized. Examples thereof include: (1) fatty acid, aliphatic alcohol, fatty acid amide, and fatty acid ether having 6 to 20 carbon chains (they may be saturated or unsaturated and may be cyclic, linear, or branched); (2) aromatic organic acids, aromatic alcohol, aromatic organic acid ester, and ether; and (3) lactic acid esters, acetic acid esters, monoterpene-based compounds, sesquiterpene-based compounds, Azone, Azone derivatives, glycerin fatty acid esters, propylene glycol fatty acid esters, sorbitan fatty acid esters (Span type), polysorbates (Tween type), polyethylene glycol fatty acid esters, polyoxyethylene hydrogenated castor oils (HCO type), polyoxyethylene alkyl ethers, sucrose fatty acid esters, and plant oils.

Specifically, caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, lauric diethanolamide, myristyl myristate, octyldodecyl myristate, cetyl palmitate, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, l-menthol, borneol, d-limonene, isoeugenol, isoborneol, nerol, dl-camphor, glycerin monocaprylate, glycerin monocaprate, glycerin monolaurate, glycerin monooleate, sorbitan monolaurate, sucrose monolaurate, polysorbate 20, propylene glycol monolaurate, polyethylene glycol monolaurate, polyethylene glycol monostearate, polyoxyethylene oleyl ether, polyoxyethylene lauryl ether, HCO-60, pirotiodecane, and olive oil are preferable. Among them, oleic acid, lauryl alcohol, myristyl alcohol, oleyl alcohol, isostearyl alcohol, lauric diethanoiamide, l-menthol, glycerin monocaprylate, glycerin monocaprate, glycerin monooleate, sorbitan monolaurate, propylene glycol monolaurate, polyoxyethylene oleyl ether, polyoxyethylene lauryl ether, and pirotiodecane are more preferable. Oleic acid, oleyl alcohol, and l-menthol are preferably used.

The adhesive layer in the adhesive preparation of the present invention may further contain a plasticizer. Examples of such a plasticizer include liquid paraffin, petroleum-based oils (e.g., paraffin-based process oil, naphthene-based process oil, and aromatic process oil), squalane, squalene, plant oils (e.g., olive oil, camellia oil, castor oil, tall oil, and peanut oil), silicone oil, dibasic acid ester (e.g., dibutyl phthalate and dioctyl phthalate), liquid rubbers (e.g., polybutene and liquid isoprene rubbers), and glycol salicylate. Among them, liquid paraffin and liquid polybutene are preferably used.

A mixture of two or more kinds of such plasticizers may be used. The content of the plasticizer based on the whole composition constituting the adhesive is appropriately determined within the range of 5 to 70% by mass, more preferably 10 to 60% by mass, particularly preferably 10 to 50% by mass, with respect to the total mass of the adhesive layer in consideration of maintaining sufficient permeability and sufficient cohesion as the adhesion preparation.

Moreover, the adhesive layer in the adhesive preparation of the present invention may be further supplemented with an antioxidant, a filler, a crosslinking agent, a preservative, a UV absorber, or the like, if necessary. Tocopherol and ester derivatives thereof, ascorbic acid, ascorbyl stearate, nordihydroguaiaretic acid, dibutylhydroxytoluene (BHT), butylated hydroxyanisole, and the like are desirable as such an antioxidant. Calcium carbonate, magnesium carbonate, silicate (e.g., aluminum silicate and magnesium silicate), silicic acid, barium sulfate, calcium sulfate, calcium zincate, zinc oxide, titanium oxide, and the like are desirable as the filler. Amino resins, phenol resins, epoxy resins, alkyd resins, thermosetting resins (e.g., unsaturated polyester), isocyanate compounds, block isocyanate compounds, organic crosslinking agents, and inorganic crosslinking agents (e.g., metals and metal compounds) are desirable as the crosslinking agent. Ethyl parahydroxybenzoate, propyl parahydroxybenzoate, butyl parahydroxybenzoate, and the like are desirable as the preservative. p-aminobenzoic acid derivatives, anthranilic acid derivatives, salicylic acid derivatives, coumarin derivatives, amino acid-based compounds, imidazoline derivatives, pyrimidine derivatives, dioxane derivatives, and the like are desirable as the UV absorber.

The adhesive layer is appropriately supplemented with such an antioxidant, a filler, a crosslinking agent, a preservative, or a UV absorber within the range of 0.01 to 10% by mass, more preferably 0.1 to 5% by mass, particularly preferably 0.2 to 2% by mass, with respect to the total mass of the adhesive preparation.

Moreover, the adhesive preparation of the present invention may further comprise, in addition to the support and the adhesive layer, a layer of a release coating that is peeled off in use. Such an adhesive preparation is easily produced, stored, and used and is therefore preferable. Examples of the release coating used in the present invention include release paper, cellophane, and synthetic resin films (e.g., polyethylene, polypropylene, polyester, polyvinyl chloride, and polyvinylidene chloride) subjected to release treatment (e.g., silicone treatment).

Next, a method for producing the adhesive preparation of the present invention will be described.

The adhesive preparation of the present invention can be produced by, but not particularly limited to, a so-called solvent or hot melt method. In the solvent method, the components of the adhesive including the drug are first added at their respective proportions to an organic solvent such as hexane, toluene, or ethyl acetate, and the mixture is stirred to obtain a uniform dissolved matter. Next, this dissolved matter is expanded onto a support and then dried with a drier to remove the organic solvent by volatilization. Then, the dissolved matter is covered with a release coating. Or otherwise, the dissolved matter is expanded onto a release coating and then dried with a drier to remove the organic solvent by volatilization. Then, the dissolved matter may be transferred to a support by compression.

In the hot melt method, the ingredients constituting the adhesive, except for the drug, are first heat-mixed at their respective proportions under temperature conditions of 150 to 200° C. in an inactive (e.g., nitrogen) atmosphere. Then, the drug is added thereto, and the mixture is stirred to obtain a uniform melt. This melt is directly expanded onto a support and covered with a release coating. Then, the resulting product is cut into a desired shape. Or otherwise, this melt is temporarily expanded onto a release coating and is allowed to further cover a support. Then, the melt is transferred onto the support by compression. Then, the resulting product may be cut into a desired shape. The hot melt method is preferably used in terms of good energy efficiency and being preferable for workers' health or environment.

It is preferred that the thickness (exclusive of the thicknesses of the support and the release coating) of the adhesive layer in the adhesive preparation should be 50 to 300 µm, more preferably 80 to 200 µm. If the thickness is less than 50 µm, the duration of adhesion or adhesiveness tends to be reduced. On the other hand, if the thickness exceeds 300 µm, cohesion and shape retention tend to be reduced.

Moreover, it is preferred that the adhesive layer should be formed such that the application amount of the adhesive layer (amount of inunction) is 80 to 210 g/m², more preferably 100 to 200 g/m², even more preferably 120 to 180 g/m², on the support.

The order described above in which each base ingredient, the drug, and other additive ingredients are added in the production method is merely taken as an example. The method for producing the adhesive preparation is not intended to be limited to the method with this order of addition.

Next, the moisture permeability of the adhesive preparation of the present invention will be described.

It is preferred that the moisture permeability should be 1 to 350 g/m²·24 hr, when measured under conditions involving a temperature of 40° C. and a relative humidity of 90% according to the method specified by JIS Z 208. If the moisture permeability falls within this range, the volatile methyl salicylate and the l-menthol that may be added thereto are difficult to volatilize and are stably maintained in the adhesive layer. Therefore, an effective amount of the drug can be locally percutaneously absorbed, when the adhesive preparation is applied to the skin. On the other hand, the adhesive preparation itself exhibits moisture permeability to some extent. Therefore, even when the adhesive preparation is applied to the affected part, moisture such as sweating in this part is moderately evaporated. Therefore, it is considered that the adhesive preparation can be applied to the skin for 24 hours or longer. As a result, the methyl salicylate can be administered more continuously. Moreover, the moisture permeability is more preferably 1 to 200 g/m²·24 hr, even more preferably 1 to 100 g/m²·24 hr, from the viewpoint of being capable of further exerting the effects described above.

The moisture permeability of the adhesive preparation of the present invention depends on the thickness of the plaster and the degree of compression in the production of the adhesive preparation. Those skilled in the art can appropriately control the moisture permeability to fall within the range described above.

Furthermore, the plasma $AUC_{0-24}$ and $C_{max}$ of the drug obtained when the adhesive preparation of the present invention is percutaneously administered in an amount of inunction of 50 to 300 g/m² to a 280-cm² area of a human for 8 hours will be described.

In the adhesive preparation of the present invention supplemented with 10% or more of methyl salicylate with respect to the total mass of the adhesive layer, the $AUC_{0-24}$ of the methyl salicylate and its metabolite salicylic acid ranges from 3.0 to 60.0 ng·hr/mL and 5000 to 13000 ng·hr/mL, respectively, preferably 13.0 to 48.0 ng·hr/mL and 6300 to 11000 ng·hr/mL, respectively, more preferably 20.0 to 40.0 ng·hr/mL and 7400 to 10000 ng·hr/mL, respectively, in terms of a mean±standard deviation under the application conditions described above. Moreover, in this case, the $C_{max}$ of the methyl salicylate and the salicylic acid ranges from 2.0 to 40.0 ng/mL and 700 to 2000 ng/mL, respectively, preferably 9.0 to 34.0 ng/mL and 900 to 1700 ng/mL, respectively, more preferably 14.0 to 28.0 ng/mL and 1100 to 1500 ng/mL, respectively, in terms of a mean±standard deviation. Moreover, when the adhesive preparation is supplemented with 1% by mass or more of l-menthol with respect to the total mass of the adhesive layer, the $AUC_{0-24}$ and $C_{max}$ of the l-menthol range from 30.0 to 130.0 ng·hr/mL and 5.0 to 20.0 ng/mL, respectively, preferably 53.0 to 110.0 ng·hr/mL and 8.0 to 17.0 ng/mL, respectively, more preferably 65.0 to 100.0 ng·hr/mL and 10.0 to 15.0 ng/mL, respectively, in terms of a mean±standard deviation under the application conditions described above.

According to the adhesive preparation of the present invention, the parameters within the ranges described above can be obtained. The $AUC_{0-24}$ and $C_{max}$ depend on the area of the adhesive preparation, the thickness of the plaster, and an individual difference between test subjects. Those skilled in the art can appropriately control the parameters to fall within the predetermined numerical ranges by use of the adhesive preparation of the present invention. Alternatively, when the adhesive preparation of the present invention is applied to 70 $cm^2$ or other areas for 8 hours, it is obvious that the AUC and $C_{max}$ get smaller according to the administration area. Moreover, the parameters described above are values obtained by use of the adhesive preparation, and these values are determined by subtracting the value of methyl salicylate, salicylic acid, or l-menthol before application mixed in daily necessities or the like.

Hereinafter, the present invention will be described more specifically with reference to Examples. However, the present invention is not intended to be limited to these Examples.

EXAMPLES

Examples 1 to 3

Production of Adhesive Preparation

Supports used in Examples 1 to 3 are respectively an interlock woven fabric of polyethylene terephthalate. Ingredients in each adhesive layer and their proportions are shown in Table 1 below.

TABLE 1

| Name of ingredient | Example 1 | Example 2 | Example 3 |
|---|---|---|---|
| Methyl salicylate | 10 | 12 | 15 |
| l-menthol | 3.0 | 3.5 | 4.5 |
| Styrene-isoprene-styrene block copolymer | 25 | 30 | 30 |
| Polyisobutylene | 10 | 10 | 10 |
| Liquid paraffin | 35 | 25 | 20 |
| Alicyclic saturated hydrocarbon resin (Arkon P-100) | 17 | 19.5 | 20.5 |
| Total | 100 | 100 | 100 |

The components shown in Table 1, except for the drug, were first heat-mixed at their respective proportions at 150 to 200° C. in an inactive (e.g., nitrogen) atmosphere. Then, the drug was added thereto, and the mixture was stirred to obtain a uniform melt. Next, this melt was temporarily expanded uniformly onto a release coating and was allowed to further cover a support. Then, the melt was transferred onto the support by compression to form an adhesive layer (amount of inunction: 120 $g/m^2$) on the support. Then, the resulting product was cut into a 280 $cm^2$ square to produce an adhesive preparation.

Example 4

Measurement of Moisture Permeability

The moisture permeability of the adhesive preparations of Examples 1 and 3 was measured at a temperature of 40° C. and a relative humidity of 90% according to the cup method (JIS Z0208).

Test pieces (n=3) used were obtained by stamping the adhesive preparations produced according to Examples 1 and 3 into a round shape of approximately 70 mm in diameter. A moisture absorbent used was anhydrous calcium chloride (which has a particle size that passes through a 2380 μm standard sieve but remains on a 590 μm standard sieve). A cup used was Y.S.S Tester No. 3525 (Yasuda Seiki Seisakusho, Ltd.).

A glass dish containing the moisture absorbent was placed in the cup, and this cup was placed on a cup table kept in a horizontal position. The test piece was placed over the cup at a position concentric with the cup, with the support in the adhesive preparation turned up. A guide was put on the cup such that the guide fitted in a groove of the cup table. A ring was forced thereinto along with the guide until the test piece came into tight contact with the upper edge of the cup. A weight was placed thereon. Then, the guide was removed by vertically pulling it up with care not to move the ring. Next, the cup was horizontally rotated, while a molten sealing wax was poured into the groove on the periphery of the cup to seal the edge of the test piece. After the sealing wax was solidified, the weight and the cup table were removed to obtain samples (n=3).

The initial mass of the cup was measured. Then, the sample was left in a thermo-hygrostat kept under test conditions involving a temperature of 40° C. and a relative humidity of 90% and taken out the sample after 24 hours. The sample was stored in a desiccator for 30 minutes and weighed. This procedure was repeated twice to measure the mass of the cup. A value obtained by subtracting the initial mass from this mass was defined as an amount of increase in mass. The amount of increase in mass converted to a value per $m^2$ was used as moisture permeability ($g/m^2 \cdot 24$ h).

As a result, the moisture permeability of the adhesive preparations of Examples 1 and 3 was 5 to 120 $g/m^2 \cdot 24$ h and 5 to 185 $g/m^2 \cdot 24$ h, respectively.

Example 5

Measurement of Plasma Concentration

The 280-$cm^2$ adhesive preparation (methyl salicylate: 336 mg; l-menthol: 100 mg) of Example 1 was applied to seven healthy adults for 8 hours. Blood was collected over time. The blood collection was performed on each of 0, 0.5, 1, 2, 3, 4, 6, 8, 10, 12, 18, and 24 hours from the start of the application, and the amount of blood collected each time was 7 mL. Methyl salicylate and l-menthol are contained in large amounts in daily necessities. Therefore, the use of such daily necessities was avoided before and during the application.

The plasma concentrations of the methyl salicylate, its metabolite salicylic acid, and the l-menthol were separately measured. The measurement was performed by liquid chromatography-mass spectrometry for the salicylic acid and by gas chromatography-mass spectrometry for the methyl salicylate and the l-menthol. Each of the measurement methods was validated beforehand to confirm measurement reliability. Values obtained by subtracting an endogenous concentration (measurement value on 0 hour) before the application from an actual measurement value were used as plasma concentrations during the application. The $C_{max}$ and $AUC_{0-24}$ were calculated according to the standard methods.

Figure 2:
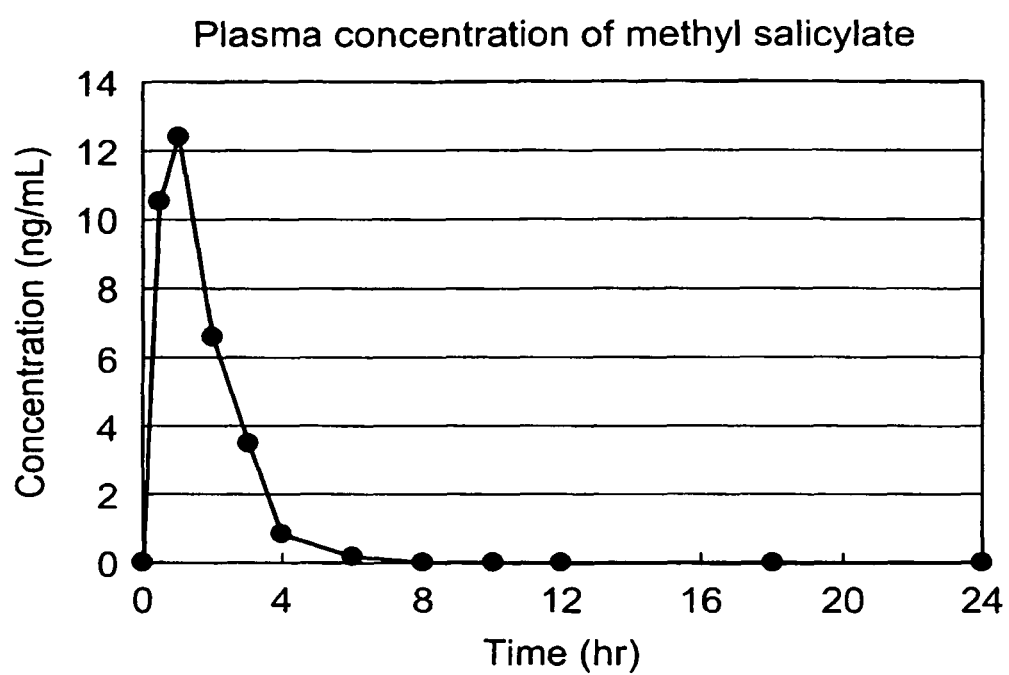
FIG. 2 is a diagram showing changes in the plasma concentration of methyl salicylate over time.
Figure 3:
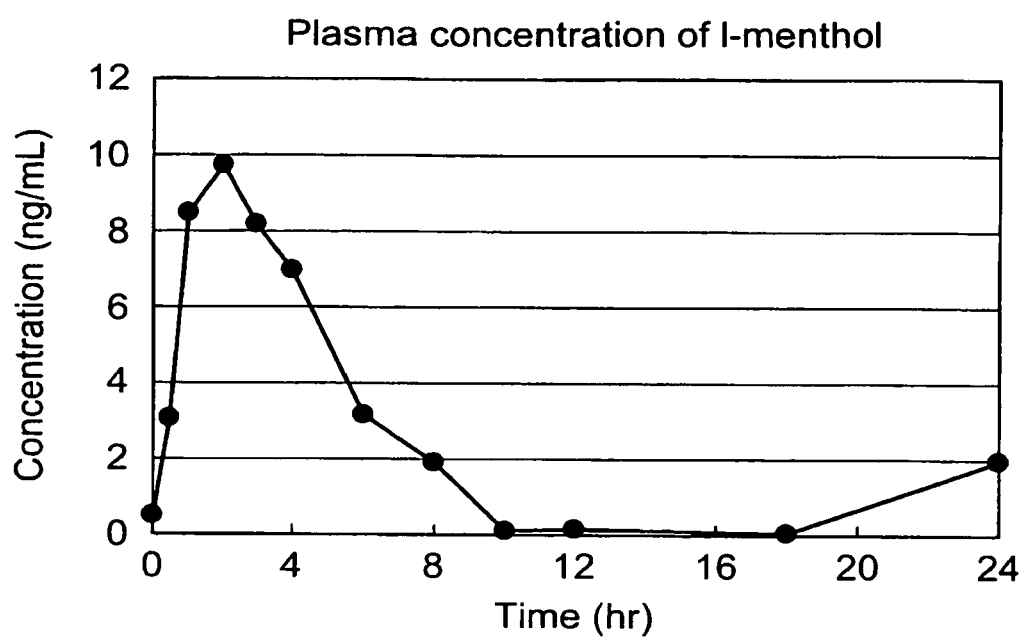
FIG. 3 is a diagram showing changes in the plasma concentration of l-menthol over time.

Changes in the plasma concentrations of the salicylic acid, the methyl salicylate, and the l-menthol over time are shown in FIGS. 1 to 3. Their respective pharmacokinetic parameters are shown in Table 2. A mean was an average value from the seven individuals to be tested. This measurement of the plasma concentrations was performed according to the guideline of FDA (U.S. Food and Drug Administration) (Guidance for Industry=Bioanalytical Method Validation).

TABLE 2

|  |  | $AUC_{0-24}$ (ng · hr/mL) | Cmax (ng/mL) |
|---|---|---|---|
| Salicylic acid | Mean ± S.D. | 6255 ± 2706 | 1078 ± 409 |
|  | Minimum value | 3948 | 705 |
|  | Maximum value | 11769 | 1771 |
| Methyl salicylate | Mean ± S.D. | 24.9 ± 14.3 | 14.6 ± 10.9 |
|  | Minimum value | 8.1 | 3.5 |
|  | Maximum value | 50.0 | 33.0 |
| l-menthol | Mean ± S.D. | 53.6 ± 33.4 | 10.7 ± 6.4 |
|  | Minimum value | 15.4 | 4.5 |
|  | Maximum value | 109 | 22.5 |

When each of the plasma parameters thus obtained is compared with a value obtained by subtracting a value on 0 hour from the plasma concentration of methyl salicylate or menthol measured in Non-Patent Document 1, the $C_{max}$ and $AUC_{0-24}$ of the methyl salicylate and the menthol in the applied 280 cm² of adhesive preparation (methyl salicylate: 336 mg; l-menthol: 100 mg) of the present invention were close to values of eight adhesive preparations (methyl salicylate: 74.88 mg×8=599 mg; menthol: 37.44×8=299.5 mg) applied in Non-Patent Document 1. This demonstrated that according to the adhesive preparation of the present invention, the sufficient plasma concentration of each active ingredient is obtained. It is considered that the local percutaneous absorption of the active ingredient is also sufficient by virtue of the adhesive preparation of the present invention. Thus, it is considered that the adhesive preparation of the present invention improves local anti-inflammatory analgesic effects.

Example 6

Measurement of Plasma Concentration

A similar experiment to that in Example 5 was conducted on 101 healthy adults. As a result, the methyl salicylate had an $AUC_{0-24}$ of 139.0 ng·hr/mL as a maximum value, 3.7 ng·hr/mL as a minimum value, and 30.1 ng·hr/mL as a mean and a $C_{max}$ of 109.4 ng/mL as a maximum value, 2.5 ng/mL as a minimum value, and 21.1 ng/mL as a mean (however, the $AUC_{0-24}$ of the methyl salicylate was a measurement result from 48 out of the 101 individuals). Moreover, the salicylic acid had an $AUC_{0-24}$ of 24731 ng·hr/mL as a maximum value, 3464 ng·hr/mL as a minimum value, and 8848 ng·hr/mL as a mean and a $C_{max}$ of 4100 ng/mL as a maximum value, 531 ng/mL as a minimum value, and 1291 ng/mL as a mean. Furthermore, the l-menthol had an $AUC_{0-24}$ of 273.0 ng·hr/mL as a maximum value, 11.1 ng·hr/mL as a minimum value, and 80.6 ng·hr/mL as a mean and a $C_{max}$ of 51.0 ng/mL as a maximum value, 2.6 ng/mL as a minimum value, and 12.4 ng/mL as a mean. Their respective pharmacokinetic parameters are shown in Table 3. This measurement of the plasma concentrations was performed according to the guideline of FDA (U.S. Food and Drug Administration) (Guidance for Industry=Bioanalytical Method Validation).

TABLE 3

|  |  | $AUC_{0-24}$ (ng * hr/mL) | Cmax (ng/mL) |
|---|---|---|---|
| Salicylic acid | Mean ± S.D. | 8848 ± 3684 | 1291 ± 543 |
|  | Minimum value | 3464 | 531 |
|  | Maximum value | 24731 | 4100 |
| Methyl salicylate | Mean ± S.D. | 30.1 ± 25.6 | 21.1 ± 18.2 |
|  | Minimum value | 3.7 | 2.5 |
|  | Maximum value | 139.0 | 109.4 |
| l-menthol | Mean ± S.D. | 80.6 ± 41.2 | 12.4 ± 6.7 |
|  | Minimum value | 11.1 | 2.6 |
|  | Maximum value | 273.0 | 51.0 |

The adhesive preparation of Example 1 could firmly follow the skin without coming off or dropping off and caused no irritation to the skin when applied thereto for 8 hours.

The invention claimed is:

1. An adhesive preparation comprising:
   a stretchable support and an adhesive layer,
   wherein the adhesive layer is laminated on at least one side of the support and comprises a thermoplastic elastomer, and 10% by mass or more of methyl salicylate with respect to the total mass of the layer,
   wherein the whole adhesive preparation has moisture permeability of 1 to 350 g/m²·24 hr measured at a temperature of 40° C. and a relative humidity of 90%, and
   wherein the methyl salicylate has a plasma $AUC_{0-24}$ per unit area ranging from $1.0 \times 10^{-2}$ to $2.1 \times 10^{-1}$ ng·hr/mL/cm² in terms of a mean±standard deviation, and a salicylic acid as a metabolite of the methyl salicylate has a plasma $AUC_{0-24}$ per unit area ranging from 17.8 to 46.4 ng·hr/mL/cm² in terms of a mean±standard deviation, when the adhesive preparation is applied to a human skin for 8 hours such that an application amount of the adhesive layer is 50 to 300 g/m².

2. The adhesive preparation according to claim 1, wherein adhesive layer contains 1% by mass or more of l-menthol with respect to the total mass of the layer.

3. The adhesive preparation according to claim 2, wherein the l-menthol has a plasma $AUC_{0-24}$ per unit area ranging from $1.0 \times 10^{-1}$ to $4.6 \times 10^{-1}$ ng·hr/mL/cm² in terms of a mean±standard deviation, and a plasma $C_{max}$ per unit area ranging from $1.7 \times 10^{-2}$ to $7.1 \times 10^{-2}$ ng/mL/cm² in terms of a mean±standard deviation, when the adhesive preparation is applied to a human skin for 8 hours such that an application amount of the adhesive layer is 50 to 300 g/m².

4. The adhesive preparation according to claim 1, wherein the adhesive layer comprises a tackifier.

5. The adhesive preparation according to claim 4, wherein the tackifier comprises one or more selected from the group consisting of a rosin-based resin and a petroleum-based resin.

6. The adhesive preparation according to claim 4, wherein the tackifier is present in the adhesive preparation from 10% by mass to 30% by mass with respect to the total mass of the adhesive layer.

7. The adhesive preparation according to claim 1, wherein the stretchable support comprises a longitudinal modulus of 2 to 12 N/5 cm and a lateral modulus of 2 to 8 N/5 cm.

8. The adhesive preparation according to claim 1, wherein the stretchable support comprises a weight per unit area of 80 to 150 g/m².

9. The adhesive preparation according to claim 1, wherein the stretchable support comprises an interlock woven fabric.

10. The adhesive preparation according to claim 1, wherein the methyl salicylate has a plasma $C_{max}$ per unit area ranging from $7.1 \times 10^{-3}$ to $1.4 \times 10^{-1}$ ng/mL/cm$^2$ in terms of a mean±standard deviation, and the salicylic acid has a plasma $C_{max}$ per unit area ranging from 2.5 to 7.1 ng/mL/cm$^2$ in terms of a mean±standard deviation, when the adhesive preparation is applied to a human skin for 8 hours such that an application amount of the adhesive layer is 50 to 300 g/m$^2$.

11. The adhesive preparation according to claim 1, wherein the thermoplastic elastomer is one or more selected from the group consisting of a styrene-isoprene-styrene block copolymer, a styrene-butadiene-styrene block copolymer, a styrene-isoprene rubber, a styrene-butadiene rubber, polyisoprene, polybutadiene, and polyisobutylene.

12. The adhesive preparation according to claim 1, wherein the thermoplastic elastomer is present in the adhesive preparation from 25% by mass to 50% by mass with respect to the total mass of the adhesive layer.

\* \* \* \* \*

UNITED STATES PATENT AND TRADEMARK OFFICE
CERTIFICATE OF CORRECTION

| | | |
|---|---|---|
| PATENT NO. | : 8,809,615 B2 | |
| APPLICATION NO. | : 12/588721 | |
| DATED | : August 19, 2014 | |
| INVENTOR(S) | : Kiyomi Tsuruda et al. | |

It is certified that error appears in the above-identified patent and that said Letters Patent is hereby corrected as shown below:

In the Claims

Claim 2, Column 14, Line 41 Between "more of" and "with respect to" please remove I-Menthol and replace it with l-Menthol, changing the Upper case I to a lower case L.

Claim 3, Column 14, Line 44 Between "wherein the" and "has a plasma" please remove I-Menthol and replace it with l-Menthol, changing the Upper case I to a lower case L.

Signed and Sealed this
Twenty-first Day of October, 2014

Michelle K. Lee
*Deputy Director of the United States Patent and Trademark Office*